United States Patent [19]

Mattson

[11] Patent Number: 4,994,039
[45] Date of Patent: Feb. 19, 1991

[54] APPARATUS AND METHOD FOR PATIENTS FROM A SINGLE DONOR OR A RESTRICTED GROUP OF DONORS

[76] Inventor: Philip D. Mattson, 1776 Plantation Way, El Cajon, Calif. 92020

[21] Appl. No.: 13,220

[22] Filed: Feb. 6, 1987

Related U.S. Application Data

[63] Continuation of Ser. No. 798,272, Nov. 15, 1985, abandoned.

[51] Int. Cl.$^5$ .............................................. A61B 19/00
[52] U.S. Cl. ..................................... 604/408; 604/410
[58] Field of Search .................. 604/408, 409, 410, 52

[56] References Cited

U.S. PATENT DOCUMENTS

| | | | |
|---|---|---|---|
| 2,950,716 | 8/1960 | Bellamy, Jr. et al. | 604/409 |
| 3,110,308 | 11/1963 | Bellamy, Jr. | 604/410 |
| 3,187,750 | 6/1965 | Tenczar, Jr. | 604/410 |
| 3,327,709 | 6/1967 | Nehring et al. | 604/409 |
| 3,870,042 | 3/1975 | Viguier | 604/410 |
| 3,911,918 | 10/1975 | Turner | 604/410 |
| 4,223,675 | 9/1980 | Williams | 604/410 |
| 4,332,122 | 6/1982 | Williams | 604/408 |
| 4,335,770 | 6/1982 | Kulle et al. | 604/408 |

Primary Examiner—John D. Yasko

[57] ABSTRACT

An apparatus for collecting, storing and providing multiple transfusions of blood in small quantities to premature infants from a single donor or a limited number of donors without wasting or discarding unused blood of such donor or donors, including a primary reservoir for collecting and storing a predetermined amount of blood from a donor, which amount is substantially less than is usually collected for adult transfusions. The apparatus is provided with a plurality of sterile, deformable satellite administering reservoirs for receiving blood from the primary reservoir in an amount corresponding to the need of the premature child. Each of the satellite reservoirs is provided with graduations thereon so that the amount of blood required by the premature infant can be collected and measured therein for subsequent transfusion to the infant. A method of providing a prolonged, continuous supply of blood for infusion to a premature infant from a single donor or a restricted number of donors is also disclosed. A first predetermined quantity of blood is collected from the donor and is stored in a sterile primary reservoir. A second and subsequent predetermined amounts of blood, corresponding to the infusion needs of the infant are withdrawn from the sterile primary reservoir into an isolated secondary reservoir without adversely affecting the remainder of the blood in the primary reservoir. The blood from the secondary reservoirs is then administered to the infant.

18 Claims, 4 Drawing Sheets

4,994,039

APPARATUS AND METHOD FOR PATIENTS FROM A SINGLE DONOR OR A RESTRICTED GROUP OF DONORS

This application is a continuation of application Ser. No. 798,272, filed Nov. 15, 1985, now abandoned.

The present invention relates generally to an apparatus for collecting blood from a single donor or restricted number of donors, storing the blood until particular quantities of it are required by the infant-patient and administering such in needed quantities to the patient without adversely affecting any remaining supplies from said single donor or restricted number of donors. The invention also relates to a method of providing a patient, such as a premature, infant with a continuous supply of blood from a single donor or a restricted number of donors whereby the blood is collected from the donor, stored until required by the patient, and administered to the patient in preselected amounts in accordance with the patient's needs without adversely affecting the remaining stored blood collected from said single donor or restricted number of donors.

BACKGROUND OF THE INVENTION

With recent advances in the field of neonatology (care of the newborn), a need for providing and maintaining a fresh and safe supply of blood for infants has been recognized, particularly very small premature infants whose lungs are insufficiently developed to maintain them without the aid of a respirator. Those infants, relying on the respirator to breath, require frequent tests in which minerals and oxygen levels in the blood are monitored. With such frequent drawing of blood, the premature infants quickly become anemic as their bone marrow cannot replace the blood at the rate at which it is lost.

Control of the anemia requires a continuous supply of blood of the appropriate type for administration to the infant in small doses, typically about only 10–30 ml for infants from 1 to up to 3 kg, over the period of hospitalization. For some infants, such controls over anemia must be maintained over prolonged periods according to hospital stays of up to several months.

However, up to now, the standard adult donation has consisted of 450 ml donations, greatly exceeding the premature infant's needs for any one transfusion. Thus, as blood over six days old is often considered unsatisfactory, care for such infants often necessitated wastage of blood due to the far lesser volumes of blood required by the infant per transfusion. Moreover, for those infants undergoing prolonged hospitalization, the potential for wastage of blood becomes extreme. Thus, systems were devised to provide blood for many infants within the nursery from a particular donor as such donor became available. After approximately six days, or exhaustion of this first blood supply, a new donor was required to be called to provide new supplies of blood for the infants. It is apparent that these systems have the disadvantage that many infants requiring prolonged hospitalizations may have received blood from possibly twenty-five different adult donors. Such greatly increased donor exposure, in turn, subjected these infants to heightened risks of allergic reactions or increased risks of exposure to hepatitis, viral infections or immune dysfunction.

U.S. Pat. No. Re. 25,129 generally recognizes the problems appurtenant to the obtaining and handling of human whole blood and particularly addresses one important problem concerning maintaining a blood supply for infants. In an effort to provide infant-sized doses, the patentee discloses a multiple compartmented bag for use in pediatric practice. The pediatric bag includes a sealed-in delivery tube for each compartment and common inlet for receiving a single adult donation of blood. The adult donation is thereby divided into five or more infant-size infusion quantities. Each of the compartments may be sealed and cut apart from the others to form self-contained bag units. However, for a 1 kg premature infant or even infants up to 2 or 3 kgs who require from only 10 to 30 ml of packed red cells, it may take up to one month or more to use up the volume of blood received from the original adult donation, while any capsules of blood remaining unused after six days might be considered unsatisfactory.

It is also known in the art to employ an apparatus including a primary reservoir bag and secondary bags for sterilely separating whole blood into its desired constituents. Thus, in U.S. Pat. No. 4,332,122, blood is collected into a primary receiving container and broken down into its constituent parts by freezing, centrifuging or other known means, after which the constituent parts may be individually transferred to secondary containers by means of a transfer tubing network.

U.S. Pat. No. 3,079,919 discloses parenteral solution equipment having a plurality of serology tubes which are filled with the donated blood so that the blood type and character can be checked prior to administration. It is suggested therein to provide the serology tube as an integral part of the main blood storage container so that the tube is always associated with the blood throughout the effective life of the blood.

SUMMARY OF THE INVENTION

The invention relates to an apparatus for collecting, storing and administering blood and particularly for receiving blood from a single adult donor or a restricted number of donors and providing a continuous, fresh supply to patients, such as premature infants. The present invention is capable of providing whole blood or any constituent thereof to an infant according to its needs. Alternatively, the apparatus is ideally suited to collecting relatively small autologous donations for administration to children or small statured adults requiring relatively small quantities of blood during any one transfusion.

The apparatus of the present invention collects and stores for administration, blood in quantities adapted to provide a continuous fresh supply of blood to infant patients in the particular amounts needed by those infants. The apparatus of the present invention also provides means to separate the blood into independent, unit-quantities useable by the infant without adversely affecting unused portions of the blood. It further permits processing of the blood to extract particular constituents of the blood especially necessary to the infant.

The apparatus of the present invention includes a primary reservoir comprising a blood bag fabricated from conventional materials. The primary bag is constructed to accept a first predetermined quantity of blood from a single donor, such quantity being substantially less than that collected by conventional blood bags accepting approximately 450 ml adult donations. Donor tubing terminating in a collection needle or collection catheter communicates with the primary bag for receiving blood from a prescreened adult donor.

A plurality of satellite bags or capsules are provided with means for selectively enabling fluid-passage communication from the primary bag to each of the satellites. Each satellite has capacity to accept a second predetermined quantity, being substantially less than said first predetermined quantity, of blood from the primary bag. The satellites are transparent and include graduations thereon for indicating the second quantity as it is received. Each satellite comprises conventional flexible material sufficiently durable to withstand centrifugation or irradiation, yet capable of being collapsed to permit aspiration of the blood or blood constituents without the need for injection of air into the satellite. Each satellite is further sterilely separable from the primary bag, separation being accomplished without adverse affect to any blood remaining in the primary bag. Thus, a second predetermined quantity of blood may be released from the primary to any or all of the satellite bags for successive administration to the infant. If necessary, before administration, the blood contained within any particular satellite may be processed by centrifugation, irradiation or the like as dictated by the needs of the infant. The graduations on each satellite, in addition to eliminating the need to weigh or estimate the quantity of blood collected therein, provide means for assisting in determining the relative concentrations of constituents in processed whole blood such as the packed cellular volume or hematocrit (HCT).

A secondary reservoir, depending from the main reservoir, may also be provided to selectively communicate therewith. The secondary reservoir is preferably of a type similar to the primary bag and selectively communicates with the primary bag for collecting blood constituents such as plasma therefrom. Thus, where the entire contents of the primary bag is to be processed into "packed" cells, the secondary bag collects and stores the residual plasma.

The apparatus of the present invention further provides a blood transfusion system for children and small adults, namely those children or adults weighing from about 60 to 100 pounds. These persons may make autologous donations, accepted by the primary bag, in amounts less than the usual adult donations, for subsequent transfusions made necessary for example, by surgery. Thus, immuno-suppressed children with leukemia or other forms of cancer could donate autologously, i.e., for one's self, or donor exposure may be limited to a compatible donor where transplantation and transfusion reaction risk are critical considerations.

The present invention also relates to a method of providing continuous supplies of fresh blood to premature infants from a single adult donor or a restricted number of adult donors wherein a first predetermined quantity of blood, being substantially less than the normal adult-size donation of approximately 450 ml, is collected from the donor. The blood is nondegeneratively stored in a common primary reservoir until a portion of it is required by the infant for infusion. Before administration to the infant, a second predetermined quantity of blood, substantially corresponding to the infusion needs of the infant, is withdrawn from such primary reservoir into a satellite reservoir through sterile connective tubing without adversely affecting any blood remaining in such primary reservoir. Afterward, the satellite is sterilely severed from the primary bag and the blood contained within such satellite is transported to the nursery for administration to the infant.

Processing of the blood contained within the satellite bag or capsule may be effected prior to administration so that particular concentrations of packed red cells, for example, may be received by the infant. Such processing is carried out while the blood remains sterilely contained within the satellite.

The method of the present invention further comprises the steps of obtaining subsequent donations of blood from said single donor or restrictive group of donors prior to exhaustion of the blood contained within the primary reservoir whenever the infant has need therefor. Where said first predetermined quantity donated equalled less than a standard adult-size donation, the donor may be at any time recalled for donating additional supplies of blood, collected within another primary reservoir for ensuring a continuous supply of fresh blood to the infant under care.

BRIEF DESCRIPTION OF THE DRAWINGS

These and other aspects and advantages of the present invention are more apparent from the following detailed description and claims, particularly when considered in conjunction with the accompanying drawings in which like parts bear like reference numerals:

DESCRIPTION OF THE PREFERRED EMBODIMENT

Figure 1:
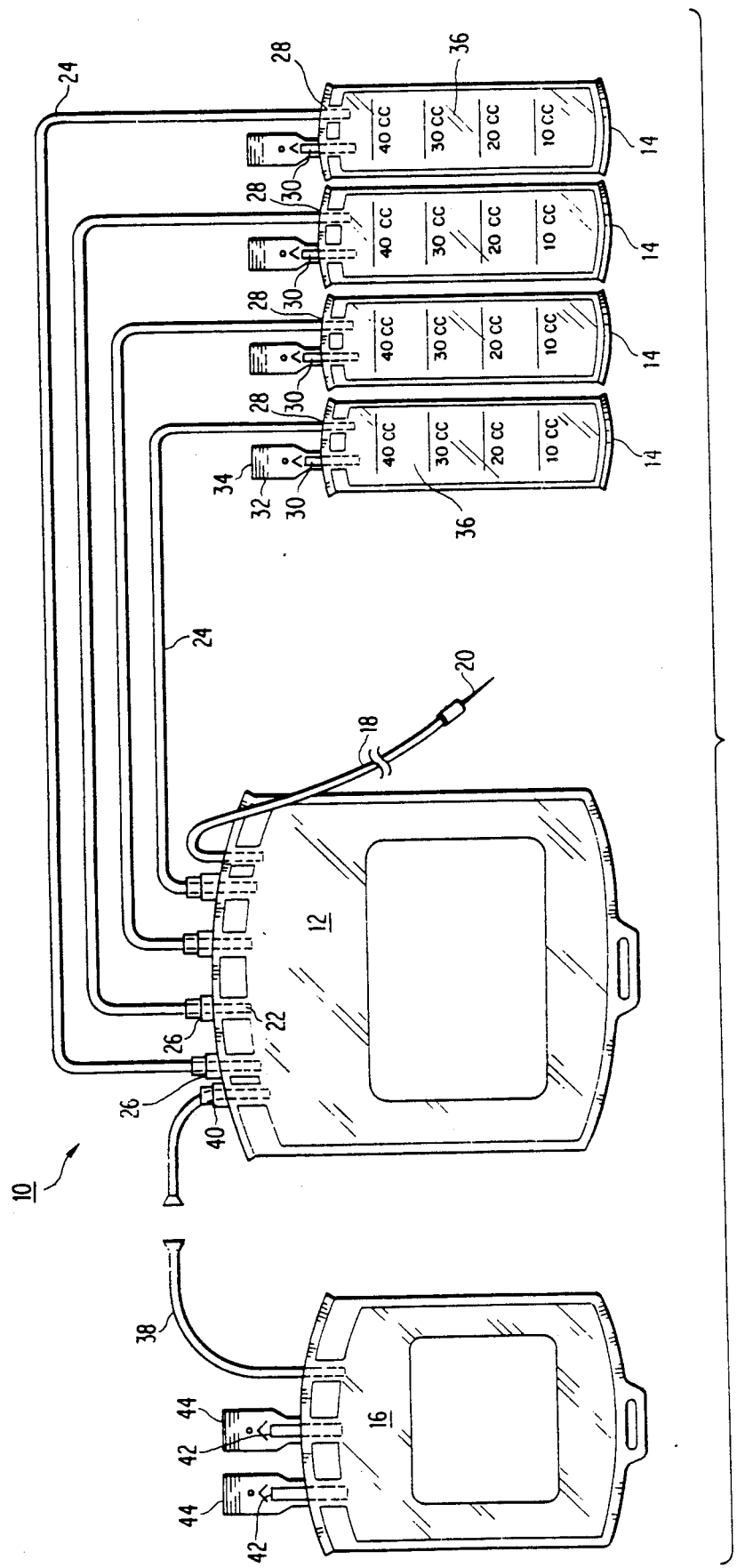
FIG. 1 is a elevational view of the system in accordance with the present invention showing a primary reservoir bag having a plurality of depending satellites and a secondary reservoir bag.

As shown in FIG. 1, an apparatus 10 for supplying continuous, fresh quantities of blood to patients such as infants from a single donor or limited number of donors includes a primary collection bag 12, a plurality of satellite bags or capsules 14 and a secondary reservoir bag 16. Primary collection bag 12 may be constructed from any conventional material well known to those skilled in the art to be inert with respect to blood collected therein. In the preferred form, primary bag 12 is of envelope or pouch-like construction having pleats or a single seam so as to collapse to a relatively flat shape when empty. Also in the preferred system, bag 12 has capacity for accepting up to about 150 ml or approximately ⅓ of the 450 ml of blood typically drawn from a designated adult-donor by conventional collection and storage systems.

Blood is collected in bag 12 from the donor by means of tubing 18 in communication with bag 12 and collection needle or catheter 20. Collection needle 20 is disposable and following collection its associated tubing 18 may be clamped and severed, or heat sealed and severed, in any well known sterile technique to remove the thereafter unnecessary tubing 18 while maintaining the sterile environment within bag 12. Before the collection of blood, bag 12 is preferably made to receive an anticoagulant to prevent coagulation of the blood while it is stored in bag 12 or transferred to any satellite 14 or to secondary reservoir 16.

Outlets 22 are provided upon bag 12 to permit liquid-passing communication with each of satellites 14. In FIG. 1, system 10 is shown as having four satellites 14, however any number may be utilized and a number of from four to six is preferred. Satellites 14 depend from primary bag 12 by means of liquid-passing tubing 24 connecting to bag 12 at outlets 22. Tubing 24 may be integral with both a satellite 14 and bag 12 or otherwise connect those receptacles in any known sterile manner. Conventional breakaway cannulas 26 selectively prevent communication between tubes 24 and bag 12 until it is desired to fill a particular satellite 14 from the contents of bag 12. Alternatively, any means, such as external obstructing clips well known in the art, may be used to selectively control the flow of fluid from bag 12 to satellites 14.

In the preferred system, satellites 14 comprise material similar to that of primary reservoir 12. It is important that satellites 14 be sufficiently durable to undergo centrifugation or irradiation yet be flexible and collapsible so as to permit aspiration of their contents without the injection of air therein. As seen in FIGS. 1, 2, 4 and 5, satellites 14 have a shape generally conforming to the wells of a conventional desk-top centrifuge.

In FIG. 1, satellites 14 each include a fluid inlet port 28 and fluid outlet port 30. Inlet port 28 is seen to comprise the end of tubing 24 terminating within each of satellites 24. Outlet ports 30 are sealed by pull-off covers 32 having finger tabs 34. In the alternative, outlets 30 could comprise sterile capped membranes for needle penetration and aspiration by syringe. Likewise, sterile connection ports such as the Luer-Lok, trademark of Becton, Dickinson & Co., would allow direct connection to the syringe for extraction of the contents.

A second predetermined amount of blood is introduced into any of satellites 14 by opening cannula 26, i.e. disrupting an internal diaphragm within tubing 14. For premature infants, this second quantity corresponds to about up to 40 ml of fluid, where the infants typically require from about from 10 ml to about 30 ml per transfusion. Graduated markings 36 on each of satellites 14 display the amount of fluid received in that satellite 14 to permit filling to the predetermined quantity appropriate for administration to the infant. Preferably, graduations 36 indicate particular aliquot quantities with respect to the 150 ml of blood originally collected in primary bag 12. After having been filled to the desired quantity as indicated by graduations 36, the satellite 14 is removed from dependence upon primary bag 12 such as for transit to the nursery. To remove a satellite 14, tubing 24 would likewise be severed following clamping or heat sealing to provide sterile decoupling of the satellite 14 without adverse affect to the remaining contents of reservoir 12.

In FIG. 1, secondary reservoir 16 depends from primary bag 12 by means of tubing 38. Tubing 38 may be integral with each, or otherwise connect bags 12 and 14. Breakaway cannula 40 likewise selectively permits fluid passage from bag 12 to secondary bag 16 upon manual manipulation of tubing 38 to rupture cannula 40. Plasma access ports 42 serve as outlets for plasma collected in secondary bag 16 as to be discussed infra and are sterilely covered by thumb-tabs 44 when not in use. It is evident to those skilled in the art that bags 12 or 16 or any of satellites 14 may include any desired number of additional access ports protectively covered by sterile tab-covers such as tab-covers 44.

Figure 2:
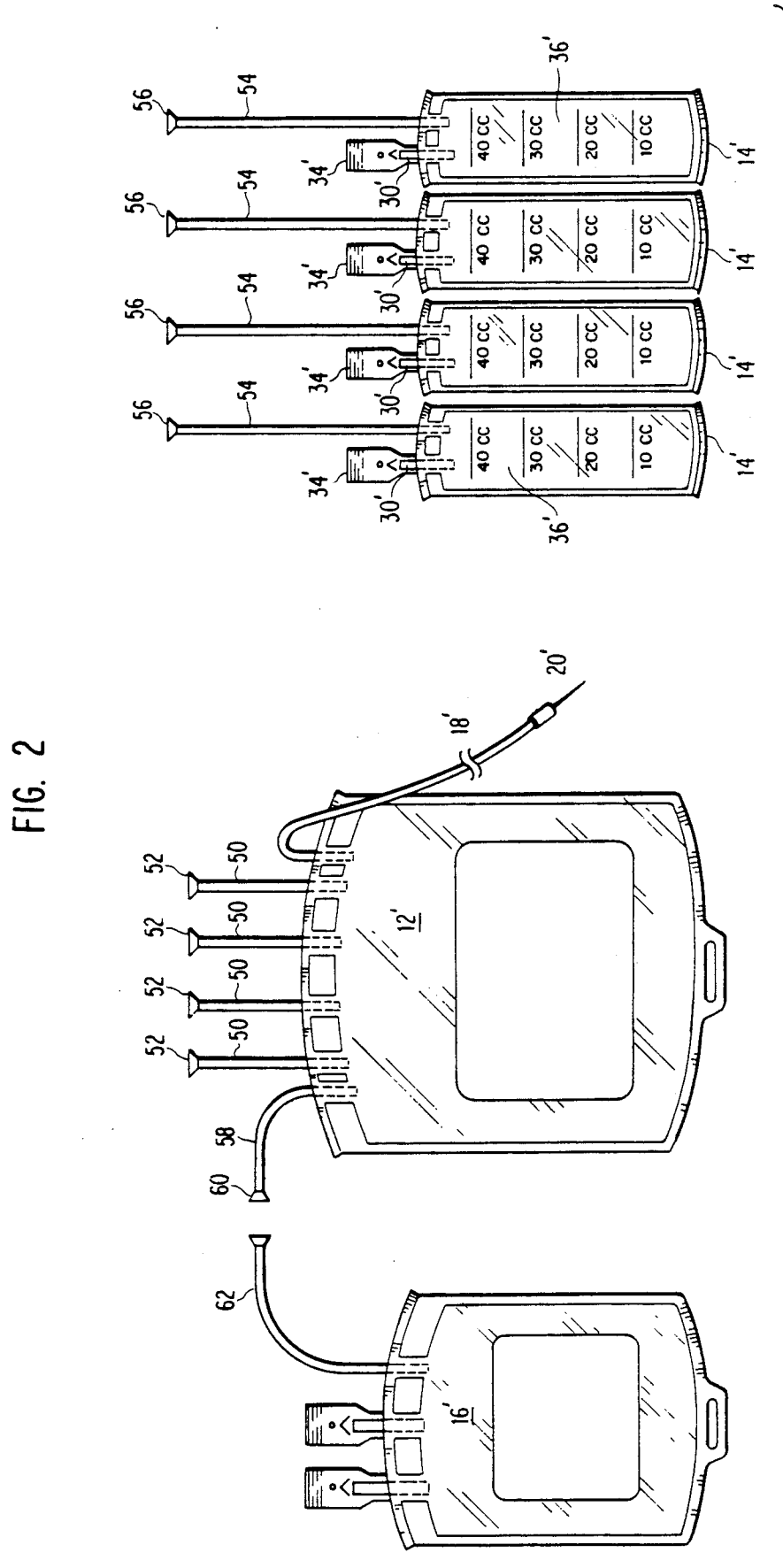
FIG. 2 is an elevational view of an alternative embodiment of the system of the present invention showing the satellite has being isolated from the primary bag and further showing pigtails on the primary bag for communicatively connecting with like pigtails on each satellite bag.

In FIG. 2 there is shown another embodiment of the present invention including a primary bag 12' preferably having construction similar to that of primary bag 12 insofar as primary bag 12' is fabricated from flexible, non-reactive material having a pleat or folds for expanding as blood is collected in bag 12' and collapsing as blood is removed. Like bag 12, bag 12' has a capacity of up to about 150 ml. Collecting needle 20' receives blood from the vein of the donor and passes it on through collecting tubing 18' to primary bag 12'.

Rather than depending from primary reservoir 12', several 40 ml capacity satellites, generally indicated by reference number 14', are normally disconnected from bag 12'. As seen in FIG. 2, bag 12' includes a plurality of "pigtails" 50, (four shown) for accommodating connection between bag 12' and each satellite 14'. "Pigtails" 50 are each shown as having a sealed distal end 52 for maintaining the environment in bag 12' in sterile condition. Sealed distal ends 52 may be prepared by the use of heat, solvent or like means known to those skilled in the art.

Satellites 14', like satellite capsules 14, are constructed from a flexible, nonreactive material capable of collapse upon aspiration of their contents. Further, like satellites 14, satellites 14' fill to assume a cylindrical shape and are sufficiently durable to be suitable for centrifuging, freezing and thawing or receiving radiation. Graduations 36' on satellites 14' provide means for quick determination of the second preselected quantity of blood to be transfused from reservoir 12' to a satellite 14'.

A corresponding pigtail 54 likewise comprising conventional connective tubing extends from satellite 14'. Before connecton to bag 12' is made, pigtails 54 are likewise in sealed-off condition at distal ends 56 to isolate the environment within satellites 14' from nonsterile environments. Access port 30' also communicates with satellite 14' and remains closed by a tab 34' until satellite 14' is required for administration to the infant.

When satellite 14' is to admit fluid from reservoir 12', two corresponding pigtails 50 and 54 being of like material and having substantially equal diameters are sterilely spliced together by means such as the sterile docking apparatus disclosed in U.S. Pat. No. 4,369,779, the entire disclosure of which is incorporated by reference herein. The apparatus disclosed in that patent acts as a hot knife splicing tubing of similar material and diameter in a substantially sterile, facilitated manner. In the alternative, other methods for making sterile connection may be used to join any pigtail 50 with a corresponding pigtail 54 as are apparent to one skilled in the art. Once having received 10 to 30 ml of fluid from bag 12', satellite 14' is sterilely decoupled from reservoir 12' by severing the connected pigtails 50 and 54 at any point along the conduit defined thereby in the above-described manner.

In FIG. 2, primary reservoir 12' is also shown as including an elongated pigtail connector 58, similarly having a sealed distal end 60, for connection, at pigtail 62, by sterile splicing or other known means to a secondary bag 16' for plasma or the like. It will be appreciated by those trained in the art that the embodiment of FIG. 2 has the advantage that while linkage from primary bag 12' to any number of satellites 14' or any number of secondary bags 16' is facilitated by pigtails 50 and 54, bag 12' when not required, may be temporarily stored without having depending bags or tubing. Thus, bag 12' may be easily stored under conditions suitable for prolonging the life of the blood or blood constituents contained therein, and temporarily disturbed for periods no longer than necessary to obtain appropriate quantities of fluid for transfusions to the infant.

Figure 3:
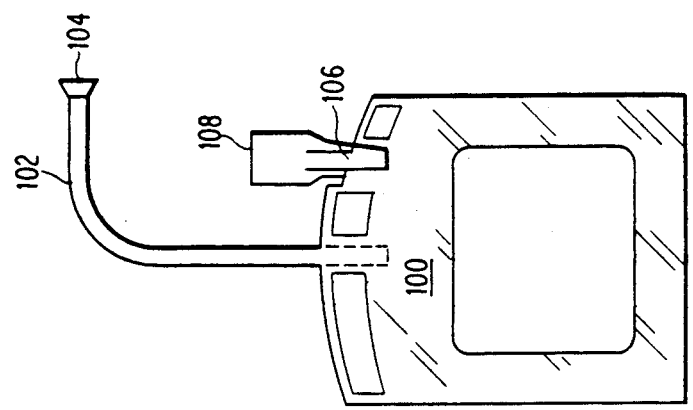
FIG. 3 is a sectional view of a mini-bag capable of storing a third quantity of blood for either direct transfusion to an infant or removal to a satellite prior to administration to the infant.

A mini-bag 100 as shown in FIG. 3 is also adapted for fluid-passing connection from primary bag 12' and may be used as a substitute in place of any of satellites 14'. Thus, mini-bag 100 is provided with a corresponding pigtail inlet 102 having sealed distal end 104 for sterile coupling with any of pigtails 50, extending from primary bag 12'. Outlet port 106 provides outward passage for fluid contained in bag 100 as required. Sterile closure tab 102 seals outlet 106 until mini-bag 124 is put to use.

Mini-bag 100 is essentially of construction similar to primary bag 12', however mini-bag 100 has a fluid capacity smaller than primary reservoir 12' but larger than satellites 14'. Thus, it is evident that mini-bag 100 can accept a third preselected quantity of fluid from primary 12', be isolated from primary bag 12' and, in turn, provide a remote reservoir for filling one or more satellites 14' thereby further reducing disturbance to the contents of primary reservoir 12'. In such an embodiment, mini-bag 100 preferably accepts a third quantity being an aliquot of the 150 ml capacity of primary bag 12' and also being a multiple of the single-infusion quantity required by the infant-patient. This quantity may be, for example, 50 ml.

Figure 4:
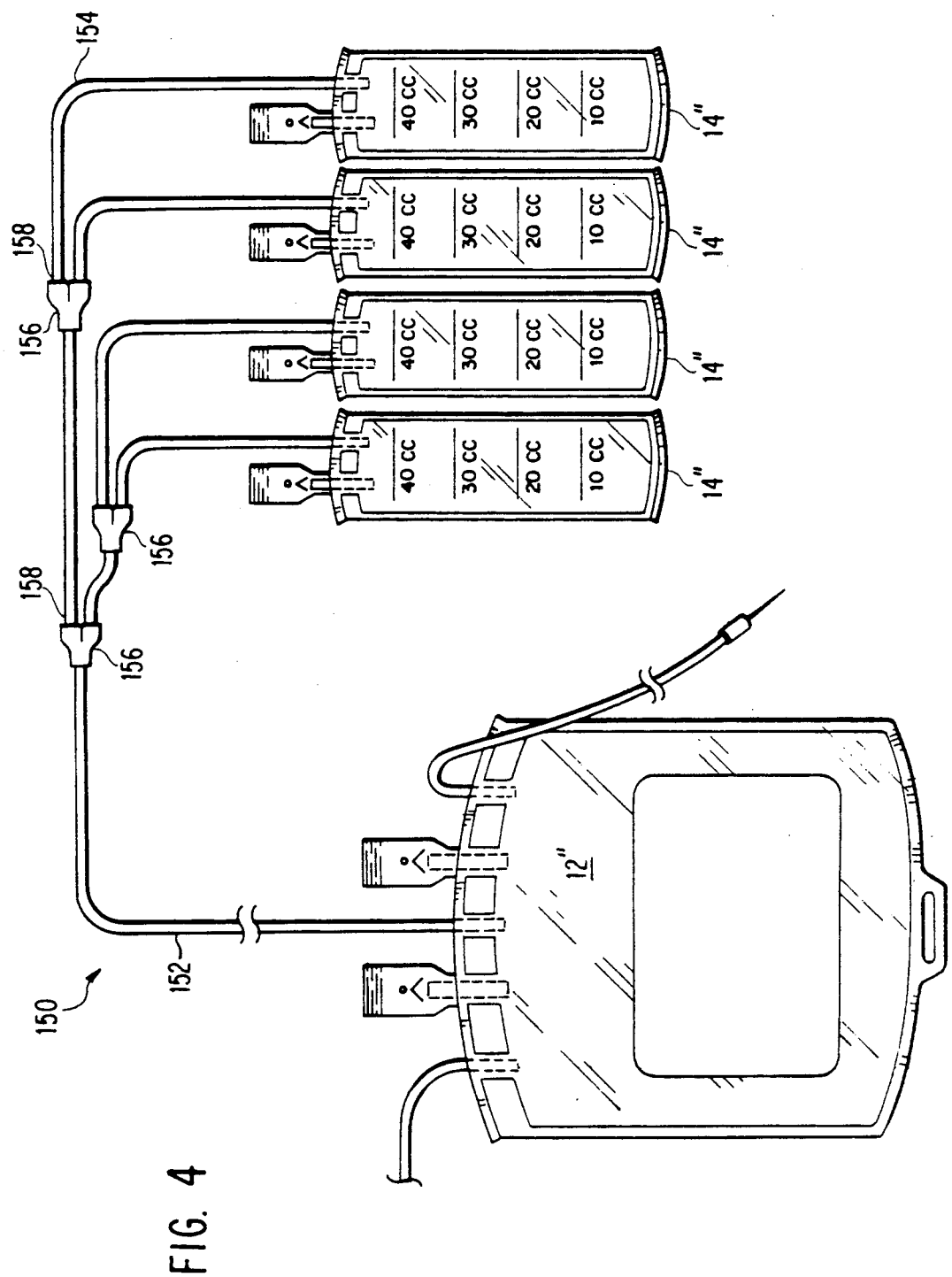
FIG. 4 is an elevational view of still another embodiment of the present invention wherein a single flow path extends and branches from the primary bag to connect with each of several satellite bags.

FIG. 4 shows still another embodiment of the present invention, similar to that shown in FIG. 1, wherein primary bag 12'' communicates with each of satellite capsules 14'' (four shown) by means of flow path 150. Flow path 150 comprises a single tube 152 for conducting fluid from primary bag 12'' to a series of branching tubes 154. As is apparent from FIG. 4, three Y-connectors 156 divide the fluid flow from outlet tube 150 into four distinct paths corresponding to the four satellites 14''. Selectively releasable closure means (not shown) such as external clips may be used for pinching off the fluid flow at the outlets 158 of any of individual Y-connectors 156 so that any of satellites 14'' may be filled from the contents of primary reservoir 12''.

It is evident to those skilled in the art that the primary bag reservoir of the present invention may be selected to contain any desired first quantity of blood for withdrawal to at least one satellite of appropriate fluid capacity. Where system 10 is dedicated to providing a continuous supply of blood for an individual premature infant, requiring prolonged hospital case, it is critical that while hospitalized, primary reservoir 12 be constructed to contain about 150 ml of blood. Alternatively, in a nursery wherein a number of infants are receiving care, but no one infant is expected to require more than very short-termed hospitalization, system 10 may be employed to provide infusion blood for all such infants requiring a particular blood-type from a single prescreened donor. Thus, the primary bag may be constructed to receive a full-size adult donation (450 ml) from a prescreened donor. An arrangement such as shown in FIG. 4, except having four such primary tubes cooperating with the primary bag could be used to fill sixteen aliquot-satellites from one primary bag containing the full-size adult donation. In such an arrangement, four groups of four aliquot-satellites could provide blood supplies to each of four infants under short-term care.

By way of example, needle 20 of system 10 enters the vein of the designated adult donor and transfers about 150 ml of blood through tubing 18 primary bag 12. Preferably, bag 12 has been made to contain an appropriate amount of anticoagulant, this amount being determined by the exact quantity of blood to be received from the donor. Within bag 12, the blood and the anticoagulant are intermixed. At this point, secondary bag 16 may be provided to collect plasma or the like through tubing 38 if it is determined that the entire contents of primary bag 12 is to undergo "packing" to produce a high erythrocyte concentration as by centrifuging. Recovery of this plasma fraction assures the same donor source in the event the infant might later require plasma for expanding blood volume or to provide clotting factors. By freezing the plasma contents of bag 16 within four hours, the plasma will be available for future use. Thus, one may generally do a light centrifugation of bag 12 to prepare an aliquot of single donor plasma and then, if desired, further concentrate the contents of the individual capsule for that particular transfusion without altering the contents of reservoir 12. This provides flexibility in preparing subsequent transfusions of lesser concentration. Furthermore, it is well known that red cell survival is better in lesser concentrated than in highly concentrated blood. Otherwise, satellites 14 will be used successively to receive fluid from bag 12 and in turn provide a source for administration to the patient.

Where system 10 is dedicated to the prolonged care of an infant, particularly a premature infant requiring frequent blood tests, it may be necessary to supply the infant with a sustained supply of small quantities of fresh blood or blood products. As each infant-size transfusion often involves only from about 10 ml to 30 ml of blood, it is evident that primary reservoir 12 need accept only a fraction of the quantity of blood normally drawn during an adult donation to supply each of exemplary satellites 14 with an appropriate quantity of blood for successive infusions to the infant. Accordingly, in the preferred system 10, primary bag 12 has a capacity of approximately only 150 ml. As shown in FIGS. 1, 2 or 4, any of satellites 14, 14', or 14'' has a total capacity of up to 40 ml, however only 10 to 30 ml would normally be transfered thereto. Thus, those skilled in the art will appreciate that since primary bag 12 collects only about 150 ml or approximately ⅓ of the normal adult donation from the prescreened donor, the same donor can be recalled for at least two more subsequent 150 ml donations without the need for waiting the often required two months before redonation. Therefore, one donor can most likely satisfy an infant's needs throughout the entire prolonged period of hospitalization.

Those skilled in the art will also appreciate that system 10 is merely exemplary and any number of satellites may be included therewith in addition to satellites 14, 16, 18 and 20, as shown.

Following the collection of 150 ml of blood in reservoir 12, system 10 can be placed in for example, a chilled or like nondegenerative environment to preserve the blood contained within bag 12. As the need for infusion arises, one of breakaway cannulas 26 is ruptured as by external hand pressure to release a predetermined quantity of fluid, typically 10-30 ml to one of satellite capsules 14. When the satellite 14 contains the appropriate quantity, tubing 24 to such satellite is severed by known sterile technique so that the satellite capsule may be transported to the nursery without disturbing the remaining contents of reservoir 12. Thereafter, an infusion from the satellite 14 may be effected by connecting satellite 14 to tubing to the donee-infant in obvious ways by means of outlet 22, after removal of tab 44.

To fully satisfy the varied and the often constantly changing needs of infants under care, system 10 is adaptable to processing whole blood to obtain various blood products for administration to the infant. For instance, for an infant undergoing hypovolemic shock, whole blood (including plasma) is preferred. Thus, the blood from satellite 14 is infused to the infant without intermediate processing.

Alternatively, if the infant is in impending heart failure compounded by very poor kidney function, concentrated red cells without excessive plasma are desirable. As such, satellite 14, being adapted for use with a conventional desk-top centrifuge, may be centrifuged just before infusion is to commence. Graduations 36 assist in determining the relative concentrations of constituents within the blood upon centrifugation. If a 40 cc aliquot in the capsule 14 were centrifuged and the plasma/red cell interface was observed to correspond to the 20 cc level, the hematocrit (HCT) or packed cellular volume would be about 50%. If the infant's condition required an HCT of 75 to 80%, then about 14 cc of plasma would be removed from satellite 14 through outlet 30 to provide the desired red cell concentration. Gentle agitation to capsule 14 would reconstitute the fluid and the packed cells could be administered to the infant without need for further testing of the specimen to ascertain the packed cell concentration.

Since satellites 14 are substantially unaffected by irradiation, intrauterine transfusions for Rh disease may be effected. Prior to the transfusion, satellite capsule 14 and its contents are irradiated to destroy lymphocytes and thereby prevent subsequent immune reactions. It is evident that the same donor providing blood for intrauterine transfers may be subsequently recalled for providing successive 150 ml donations to maintain single donor exposure should the infant require further transfusions following birth.

Figure 5:
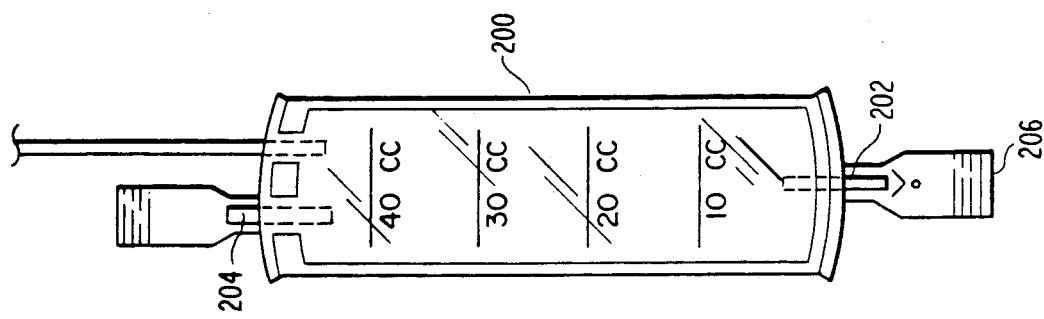
FIG. 5 is an enlarged, sectional view of an alternative preferred satellite capsule suitable for use with the systems shown in FIGS. 1, 2 or 4.

FIG. 5 illustrates an alternative satellite capsule 200 having construction identical with those of FIGS. 1 and 2 except that lower outlet 202 is provided along with upper outlet 204. When not in use, outlets 202 and 204 are sterilely covered by pull-off tabs 206.

With the capsule of FIG. 5, removal of a majority of white cells is facilitated without the need for irradiation or other special processing. Following centrifugation, the undesirable white cells commonly tend to form a layer or zone at about just above a similarly formed layer of red cells. In the satellite capsules of the present invention, this white cell layer is well defined and easily observable due to the size and shape of capsule 200. Thus, the white cell layer or zone can be extracted from the blood within capsule 200 by first centrifuging capsule 200 to form three distinct zones, an upper plasma zone, an intermediate white cell zone and a lower red cell or packed zone. Red cells are next extracted through lower outlet 202. Then an appropriate portion of plasma to afford the required HCT is obtained through top outlet 204 while the white cell layer remains in capsule 200 and may be discarded therewith. In the case of extremely premature infants an even more refined product may be desired, in which case the red blood cells are now washed. This is accomplished by adding, for example, 15 cc of sterile saline solution through outlet 204. The resulting solution is then gently agitated and recentrifuged. The product is then removed through outlet 202.

Those skilled in the art will appreciate that the appropriate quantities of packed red cells and plasma are withdrawn in accordance with graduations 208 on capsule 200 so that the proper HCT may be obtained by remixing following withdrawal of these blood products.

With any of the preferred methods of processing and administering blood with the reduced donor exposure apparatus, it is preferred that in the care of infants, one satellite capsule containing a quantity of blood equalling a full transfusion for the infant be retained in case of emergency. In the alternative, such complete transfusion could be retained within the primary reservoir. In either event, it should be apparent to obtain a subsequent donation from the original donor before resort to the emergency supply is made if it is expected that the infant's needs for infusions could persist.

While the reduced donor exposure system is particularly useful in treating infants, especially premature infants requiring prolonged hospitalization, the system of the present invention also provides means for storing, processing and administering blood to small adults or children weighing, for example, from about 60 to 100 pounds. In the treating of these patients, the present satellite units would be made unnecessary while the remaining apparatus, namely primary bag 12 in FIG. 1 and secondary bag 16 would hold an appropriate quantity of blood, normally about 150 ml, for infusion to these patients. Bag 12, containing a corresponding quantity of anticoagulant, obviates opening the system to remove excess anticoagulant.

Although the present invention has been described primarily with reference to a number of preferred embodiments, rearrangements and modifications may be made by one skilled in the art within the scope of the invention.

I claim:

1. A donor exposure limiting apparatus for providing multiple transfusions of blood to premature infants comprising:

a sterile, deformable primary reservoir having an inlet for admitting a first predetermined quantity of blood being substantially less than an adult-size donation of about 450 ml to about 550 ml from the donor into said primary reservoir;

collecting means for collecting said first predetermined quantity of blood from the donor and for conducting the blood to said inlet;

sterilely sealable outlets for releasing blood from said primary reservoir;

selectively releasable closures for preventing the release of blood from said reservoir through said outlets;

a plurality of sterile, deformable satellite administering reservoirs for receiving a second predetermined quantity of blood substantially corresponding to the infusion requirements of the premature infant from said primary reservoir and providing said second quantity to the infant, each of said satellite reservoirs having inlet means for selectively receiving said second predetermined quantity of blood from said primary reservoir, each of said satellite reservoirs having graduations thereon for visually indicating said second quantity received by said satellite reservoirs and outlet means for administering said second predetermined quantity of blood therefrom to the infant, at least one of said satellite reservoirs having top outlet means for releasing blood plasma, bottom outlet means for releasing red blood cells and a central portion between said top and bottom outlet means for containing white blood cells, whereby the blood plasma and the red blood cells are separable from the white blood cells in said at least one satellite reservoir said primary reservoir having a capacity of about 150 ml and each of said satellite reservoirs having a capacity of about 40 ml, said first predetermined quantity being about 150 ml and said second preselected quantity being from about 10 ml to about 30 ml.

2. The apparatus as claimed in claim 1 further comprising sterile flow paths between said primary reservoir and each satellite reservoir, each of said satellite reservoirs being adapted for sterile isolation from said primary reservoir after receipt of said second predetermined quantity of blood, said flow paths being adapted for sterile severing upon receipt of said second quantity of blood from said primary reservoir by any of said satellite reservoirs.

3. The apparatus as claimed in claim 2 in which each of said satellite reservoirs comprises flexible inert material being sufficiently durable to withstand centrifugation and/or irradiation with said second quantity of blood contained therein and being sufficiently flexible to permit aspiration of the blood without the injection of air into said satellite reservoir.

4. The apparatus as claimed in claim 1 in which said second predetermined quantity is an aliquot of said first quantity.

5. The apparatus as claimed in claim 2 further comprising a secondary reservoir bag being constructed similarly to said primary bag, said secondary reservoir including sterilely severable tubing for providing fluid-path communication between said primary reservoir and said secondary reservoir.

6. The apparatus as claimed in claim 1 in which said primary reservoir and said plurality of satellite administering reservoirs are isolated before receipt of said second quantity of blood by any of said satellite reservoirs, said primary reservoir further comprising pigtails and each of said satellite reservoirs further comprising corresponding pigtails communicatively connecting to said pigtails of said primary reservoir for permitting passage of said second quantity of blood from said primary reservoir to any of said secondary reservoirs.

7. The apparatus as claimed in claim 6 in which said communicatively connecting pigtails are further adapted for sterile separation after reception by said satellite reservoirs of said second quantity of blood.

8. The apparatus as claimed in claim 7 in which each of said satellite reservoirs comprises flexible nonreactant material being sufficiently durable to withstand centrifugation and/or irradiation with said second quantity of blood contained therein and being sufficiently flexible to permit aspiration of the blood without the injection of air into said satellite reservoir.

9. The apparatus as claimed in claim 6 further comprising mini-bag means for selectively receiving a third predetermined quantity of blood from said primary reservoir, said mini-bag means including pigtails, corresponding to said pigtails extending from said primary reservoir, for communicatively connecting said mini-bag means to said primary reservoir.

10. The apparatus as claimed in claim 9 in which said third predetermined quantity is less than said first preselected quantity and greater than said second predetermined quantity.

11. A method of providing a prolonged continuous supply of blood, for infusion to a premature infant, from a single donor or small group of donors, said donor and said donors in said small group of donors being capable of donating a first normal, adult-size donation of about 450 to about 550 ml of blood and being capable of subsequently donating a second normal, adult-size donation after a predetermined period, said method comprising the steps of:

(A) collecting a first predetermined quantity of blood, being substantially less than the normal, adult-size donation quantity, from said single donor or from one donor from said small group of donors, said first quantity being a fraction of the normal, adult-size donation;

(B) nondegeneratively storing said first collected quantity of blood in a primary reservoir, whereby said first quantity of blood has a normal, useful life;

(C) withdrawing a second predetermined quantity of blood, substantially corresponding to the infusion needs of the infant, from said primary reservoir into an isolated satellite reservoir without adversely affecting the blood remaining in said primary reservoir, whereby said remaining blood is depleted by an amount equal to said second quantity;

(D) administering said second quantity of blood to the infant from said satellite reservoir;

(E) recalling said donor or one of said donors from said small group of donors when the useful life of said remaining blood has expired or when said remaining blood is depleted to less than an amount equal to said second predetermined quantity;

(F) collecting another first predetermined quantity of blood from said donor or from one of said donors from said small group of donors within a period substantially less than said predetermined period between normal, adult-size donations;

(G) repeating steps (B) through (F) until the infant no longer requires infusions of blood.

12. The method as claimed in claim 11 in which said second quantity is less than said first quantity.

13. The method as claimed in claim 12 in which said first quantity is about 150 ml and said second quantity is from about 10 ml to about 30 ml.

14. The method as claimed in claim 13 further comprising the step of centrifuging said second quantity of blood in said satellite reservoir before administration to the infant.

15. The method as claimed in claim 14 further comprising the steps of removing a desired quantity of concentrated red blood cells by means of a bottom outlet in said satellite reservoir, removing a desired quantity of plasma by means of a top outlet in said satellite reservoir and remixing the red cells and the plasma for administration to the infant without need of subsequent weighing or estimating of the quantities of red cells and plasma in said mixture.

16. The method as claimed in claim 15 in which the plasma, white blood cells and the red blood cells define easily observable layers within said satellite reservoirs.

17. The method as claimed in claim 13 further comprising the step of irradiating said second quantity of blood in said satellite reservoir before administration to the infant.

18. The method as claimed in claim 12 in which an emergency quantity of blood equalling said second quantity is withdrawn to one of said satellite reservoirs and retained for emergency purposes.

* * * * *